(12) United States Patent
Young

(10) Patent No.: US 8,366,650 B2
(45) Date of Patent: Feb. 5, 2013

(54) BILIARY/PANCREATIC SHUNT DEVICE AND METHOD FOR TREATMENT OF METABOLIC AND OTHER DISEASES

(75) Inventor: Andrew Young, Rancho Santa Fe, CA (US)

(73) Assignee: Satiogen Pharmaceuticals, Inc., San Diego, CA (US)

( * ) Notice: Subject to any disclaimer, the term of this patent is extended or adjusted under 35 U.S.C. 154(b) by 808 days.

(21) Appl. No.: 12/084,069

(22) PCT Filed: Oct. 24, 2006

(86) PCT No.: PCT/US2006/041521
§ 371 (c)(1),
(2), (4) Date: Apr. 23, 2008

(87) PCT Pub. No.: WO2007/050628
PCT Pub. Date: May 3, 2007

(65) Prior Publication Data
US 2009/0264808 A1    Oct. 22, 2009

Related U.S. Application Data

(60) Provisional application No. 60/729,770, filed on Oct. 24, 2005.

(51) Int. Cl.
*A61M 5/00* (2006.01)
(52) U.S. Cl. ............... 604/8; 604/9; 623/23.68
(58) Field of Classification Search ........... 604/8, 9; 623/23.68
See application file for complete search history.

(56) References Cited

U.S. PATENT DOCUMENTS

| | | | |
|---|---|---|---|
| 4,315,509 A | 2/1982 | Smit | |
| 4,501,264 A | 2/1985 | Rockey | |
| 4,592,339 A | 6/1986 | Kuzmak et al. | |
| 5,306,300 A | 4/1994 | Berry | |
| 5,322,697 A | 6/1994 | Meyer | |
| 5,753,253 A | 5/1998 | Meyer | |
| 5,820,584 A | 10/1998 | Crabb | |
| 5,868,141 A | 2/1999 | Ellias | |
| 6,267,988 B1 | 7/2001 | Meyer | |
| 6,409,755 B1 * | 6/2002 | Vrba | 623/1.2 |
| 6,572,627 B2 | 6/2003 | Gabbay | |

(Continued)

FOREIGN PATENT DOCUMENTS

| | | |
|---|---|---|
| EP | 1273659 A1 | 1/2003 |
| EP | 1347052 A1 | 9/2003 |

(Continued)

OTHER PUBLICATIONS

Abtahi, F.S. & Djahanguiri, B. (1975) Decreased incidence of indomethacin-induced gastric ulceration in rats by bile duct diversion. Br J Surg 62, 113-4.

(Continued)

*Primary Examiner* — Leslie Deak
(74) *Attorney, Agent, or Firm* — Wilson, Sonsini, Goodrich & Rosati

(57) ABSTRACT

Provided is a shunt device that promotes stimulation of secretion of intestinal L-cells and other enteroendocrine cell types. Enteroendocrine secretion is stimulated directly or indirectly by shunting bile and/or pancreatic secretion to segments of the gut more distal than would normally occur The shunt device may be a flexible catheter that is impervious to such secretions, with a proximal end draining the pancreatic/bile duct, and a distal end residing distally within the lumen of the small or large intestine. The shunt may be inserted with minimally invasive techniques, such as by endoscopy.

30 Claims, 4 Drawing Sheets

U.S. PATENT DOCUMENTS

| | | | |
|---|---|---|---|
| 6,675,809 B2 | 1/2004 | Stack et al. | |
| 6,758,219 B2 | 7/2004 | Sapala et al. | |
| 7,314,489 B2 | 1/2008 | McKenna et al. | |
| 7,833,279 B2* | 11/2010 | Knudson et al. | 623/23.64 |
| 2002/0183826 A1 | 12/2002 | Dorn et al. | |
| 2003/0004493 A1 | 1/2003 | Casey et al. | |
| 2003/0069533 A1* | 4/2003 | Kakutani et al. | 604/8 |
| 2003/0191476 A1 | 10/2003 | Smit | |
| 2004/0015201 A1 | 1/2004 | Greenstein | |
| 2004/0039452 A1 | 2/2004 | Bessler | |
| 2004/0049209 A1 | 3/2004 | Benchetrit | |
| 2004/0089313 A1 | 5/2004 | Utley et al. | |
| 2004/0092892 A1 | 5/2004 | Kagan et al. | |
| 2004/0097989 A1 | 5/2004 | Molina Trigueros | |
| 2004/0107004 A1 | 6/2004 | Levine et al. | |
| 2004/0117031 A1* | 6/2004 | Stack et al. | 623/23.65 |
| 2004/0193092 A1 | 9/2004 | Deal | |
| 2004/0225251 A1 | 11/2004 | Glickman | |
| 2004/0249362 A1* | 12/2004 | Levine et al. | 604/523 |
| 2005/0043817 A1 | 2/2005 | McKenna et al. | |
| 2005/0085787 A1* | 4/2005 | Laufer | 604/500 |
| 2005/0096750 A1 | 5/2005 | Kagan et al. | |
| 2006/0106332 A1 | 5/2006 | Knudson et al. | |

FOREIGN PATENT DOCUMENTS

| | | |
|---|---|---|
| WO | WO 02/35980 A3 | 5/2002 |
| WO | WO-03-011179 A2 | 2/2003 |
| WO | WO 03/086246 A1 | 10/2003 |
| WO | WO 03/086247 A1 | 10/2003 |
| WO | WO 03/094785 A1 | 11/2003 |
| WO | WO 2004/019765 A2 | 3/2004 |
| WO | WO 2004/049982 A2 | 6/2004 |
| WO | WO 2004/087233 A2 | 10/2004 |

OTHER PUBLICATIONS

Adrian, T.E., Bacarese-Hamilton, A.J., Smith, H.A., Chohan, P., Manolas, K.J. & Bloom, S.R. (1987) Distribution and postprandial release of porcine peptide YY. J Endocrinol 113, 11-14.

Adrian, T.E., Ballantyne, G.H., Longo, W.E., Bilchik, A.J., Graham, S., Basson, M.D., Tierney, R.P. & Modlin, I.M. (1993) Deoxycholate is an important releaser of peptide YY and enteroglucagon from the human colon. Gut 34, 1219-1224.

Adrian, T.E., Ferri, G.L., Bacarese-Hamilton, A.J., Fuessi, H.S., Polak, J.M. and Bloom, S.R. (1985) Human distribution and release of a putative new gut hormone, peptide YY. Gastroenterology 89, 1070-1077.

Borgstrom, B. (1953) On the mechanism of the intestinal fat absorption. V. The effect of bile diversion on fat absorption in the rat. Acta Physicl Scand 28, 279-86.

Chen, F., MA, L, Dawson, P.A., Sinal, C.J., Sehayek, E., Gonzalez, F.J., Breslow, J., Ananthanarayanan, M. & Shneider, B.L. (2003) Liver receptor homologue-1 mediates species- and cell line-specific bile acid-dependent negative feedback regulation of the apical sodium-dependent bile acid transporter. J Biol Chem 278, 19909-19916.

Doty, J.E., Gu, Y.G. & Meyer, J.H. (1988) The effect of bile diversion on satiety and fat absorption from liquid and solid dietary sources. J Surg Res 45, 537-43.

Dowling, R.H., Mack, E. & Small, D.M. (1970) .Effects of controlled interruption of the enterohepatic circulation of bile salts by biliary diversion and by ileal resection on bile salt secretion, synthesis, and pool size in the rhesus monkey. J Clin Invest 49, 232-42.

Eissele, R., Goke, R., Willemer, S., Harthus, H.P., Vermeer, H., Arnold, R. & Goke, B. (1992) Glucagon-like peptide-1 cells in the gastrointestinal tract and pancreas of rat, pig and man. Eur J Clin Invest 22, 283-91.

Erlanson-Albertsson, C. and Larsson, A. (1988) The activation peptide of pancreatic procolipase decreases food intake in rats. Regul Pept 22, 325-331.

Hara, H. & Kiriyama, S. (1991) Responses of the exocrine pancreatic secretion to spontaneous feeding in rats with bile-pancreatic juice diversion. Proc Soc Exp Biol Med 198, 732-6.

Hara, H., Narakino, H. & Kiriyama, S. (1994) Enhancement of pancreatic secretion by dietary protein in rats with chronic diversion of bile-pancreatic juice from the proximal small intestine. Pancreas 9, 275-9.

Hughes, S.J., Behrns, K.E. & Sarr, M.G. (1993) Chronic bile diversion does not alter canine interdigestive myoelectric activity. Dig Dis Sci 38, 1055-61.

Huneau, J.F., ER;Anson-Albertsson, C., Beauvallet, C. & Tome, D. (1994) The in vitro intestinal absorption of enterostatin is limited by brush-border membrane peptidases. Regul Pept 54, 495-503.

Izukura, M., Hashimoto, T., Gomez, G., Uchida, T., Greeley, G.H. Jr & Thompson, J.C. (1991) Intracolonic infusion of bile salt stimulates release of peptide YY and inhibits cholecystokinin-stimulated pancreatic exocrine secretion in conscious dogs. Pancreas 6, 427-32.

Kawamata, Y., Fujii, R., Hosoya, M., Harada, M., Yoshida, H., Miwa, M., Fukusumi, S., Habata, Y., Itoh, T., Shintani, Y., Hinuma, S., Fujisawa, Y. & Fujino, M. (2003) A G protein-coupled receptor responsive to bile acids. J Biol Chem 278, 9435-9440.

Konturek, S.J. & Dubiel, J. (1969) Effect of diversion of bile and pancreatic juice on pentagastrin-produced duodenal ulcers in cats. Scand J Gastroenterol 4, 59-64.

Konturek, S.J. & Thor, P. (1973) Effect of diversion and replacement of bile on pancreatic secretion. Am J Dig Dis 18, 971-7.

Koopmans, H.S., Sclafani, A., Fichtner, C. & Aravich, P.F. (1982) The effects of ileal transposition on food intake and body weight loss in VMH-obese rats. Am J Clin Nutr 35, 284-93.

Kurosawa, H., Miyasaka, K. & Kitani, K. (1989) Influence of bile flow obstruction vs bile diversion on pancreatic secretion in the conscious rat. Int J Pancreatol 4, 187-97.

Leroux, C.W., Aylwin, S.J.B., Coyle, F., Ghatei, M., Patel, A. & Bloom, S.R. (2003) Meal-Stimulated Release of the Putatitive Satiety Hormone PYY in Severe Obesity and Following Gastric Bypass Surgery. Endocrine Society Program & Abstracts 85th Annual Meeting, Philadelphia, Jun. 19-22 105. Abstract OR33-2.

Levan, V.H. & Green, G.M. (1986) Effect of diversion of bile-pancreatic juice to the ileum on pancreatic secretion and adaptation in the rat. Proc Soc Exp Biol Med 181, 139-43.

Li, Y., Hao, Y. & Owyang, C. (1995) Evidence for autoregulation of cholecystokinin secretion during diversion of bile pancreatic juice in rats. Gastroenterology 109, 231-8.

Linke, C. (1951) The effect of diversion of bile to various parts of the intestine. Surg Forum 94, 179-83.

Lloyd, K.C., Holzer, H.H., Zittel, T.T. & Raybould, H.E. (1993) Duodenal lipid inhibits gastric acid secretion by vagal, capsaicin-sensitive afferent pathways in rats. Am J Physiol 264, G659-G663.

Maruyama, T., Miyamoto, Y., Nakamura, T., Tamai, Y., Okada, H., Sugiyama, E., Nakamura, T., Itadani, H. & Tanaka, K. (2002) Identification of membrane-type receptor for bile acids (M-BAR). Biochem Biophys Res Commun 298, 714-719.

Mei, J., Bouras, M. & Erlanson-Albertsson, C. (1997) Inhibition of insulin release by intraduodenally infused enterostatin- VPDPR in rats. Peptides 18, 651-655.

Mei, J. & Erlanson-Albertsson, C. (1996) Role of intraduodenally administered enterostatin in rats: inhibition of food. Obes Res 4, 161-165.

Naslund, E., Backman, L., Holst, J.J., Theodorsson, E. & Hellstrom, P.M. (1998a) Importance of small bowel peptides for the improved glucose metabolism 20 years after jejunoileal bypass for obesity. Obes Surg 8, 253-260.

Naslund, E., Gryback, P., Backman, L., Jacobsson, H., Holst, J.J., Theodorsson, E. & Hellstrom, P.M. (1998b) Distal small bowel hormones: correlation with fasting antroduodenal motility and gastric emptying. Dig Dis Sci 43, 945-952.

Naslund, E., Gryback, P., Hellstrom, P.M., Jacobsson, H., Holst, J.J., Theodorsson, E. & Backman, L. (1997) Gastrointestinal hormones and gastric emptying 20 years after jejunoileal bypass for massive obesity. Int J Obes Relat Metab Disord 21, 387-392.

Ohlsson, B., Yusa, T., Rehfeld, J.F., Lundquist, I., Ihse, I. & Axelson, J. (2000) Effects of intraluminal trypsin and bile on the exocrine and endocrine pancreas after pancreaticobiliary diversion and biliodigestive shunt. Pancreas 20, 170-6.

Pilichiewicz, A., O'Donovan, D., Feinle, C., Lei, Y., Wishart, J.M., Bryant, L., Meyer, J.H., Horowitz, M. & Jones, K.L. (2003) Effect of lipase inhibition on gastric emptying of, and the glycemic andincretin responses to, an oil/aqueous drink in type 2 diabetes mellitus. J Clin Endocrinol Metab 88, 3829-3834.

Plaisancie, P., Dumoulin, V., Chayvialle, J.A. & Cuber, J.C. (1995) Luminal glucagon-like peptide-1 (7-36) amide-releasing factors in the isolated vascularly perfused rat colon. J Endocrinol 145, 521-526.

Plaisancie, P., Dumoulin, V., Chayvialle, J.A. & Cuber, J.C. (1996) Luminal peptide YY-releasing factors in the isolated vascularly perfused rat colon. J Endocrinol 151, 421-9.

Raybould, H.E. (1999) Nutrient tasting and signaling mechanisms in the gut. I. Sensing of lipid by the intestinal mucosa. Am J Physiol 277, G751-G755.

Rhodes, J., Davies, H.A., Wheeler, M.H., Psaila, J., Newcombe, R.G., Jones, J.M. & Bloom, S. (1984) Bile diversion from the duodenum: its effect on gastric and pancreatic function. Scand J Gastroenterol Suppl 92, 221-3.

Sorhede, M., Erlanson-Albertsson, C., Mei, J., Nevalainen, T., Aho, A. & Sundler, F. (1996) Enterostatin in gut endocrine cells—immunocytochemical evidence. Peptides 17, 609-614.

Sorhede, M., Mei, J. & Erlanson-Albertsson, C. (1993) Enterostatin: a gut-brain peptide regulating fat intake in rat. J Physiol Paris 87, 273-275.

Spannagel, A.W., Green, G.M., Guan, D., Liddle, R.A., Faull, K. & Reeve, J.R. Jr (1996) Purification and characterization of a luminal cholecystokinin-releasing factor from rat intestinal secretion. Proc Natl Acad Sci U S A 93, 4415-4420.

Spannagel, A.W., Reeve, J.R. Jr, Greeley, G.H. Jr, Yanaihara, N., Liddle, R.A. & Green, G.M. (1998) Bioactivity of intraduodenally and intravenously infused fragments of luminal cholecystokinin' releasing factor (LCRF). Regul Pept 73, 161-164.

Spannagel, A.W., Reeve, J.R. Jr, Leddle, R.A., Guan, D. & Green, G.M. (1997) An amino-terminal fragment of LCRF, LCRF- (1-35), has the same activity as the natural peptide. Am J Physiol 273, G754-G758.

Takahashi, M., Naito, H., Sasaki, I., Funayama, Y., Shibata, C. & Matsuno, S. (2004) Long-term bile diversion enhances basal and duodenal oleate-stimulated pancreatic exocrine secretion in dogs. Tohoku J Exp Med 203, 87-95.

Tarasova, N., Spannagel, A.W., Green, G.M., Gomez, G., Reed, J.T., Thompson, J.C., Hellmich, M.R., Reeve, J.R. Jr, Liddle, R.A. & Greeley, G.H. Jr (1997) Distribution and localization of a novel cholecystokinin-releasing factor in the rat gastrointestinal tract. Endocrinology 138, 5550-5554.

Wang, Y., Prpic, V., Green, G.M., Reeve, J.R. Jr & Liddle, R.A. (2002) Luminal CCK-releasing factor stimulates CCK release from human intestinal endocrine and STC-1 cells. Am J Physiol Gastrointest Liver Physiol 282, G16-G22.

Wu, S.V., Rozengurt, N., Yang, M., Young, S.H., Sinnett-Smith, J. & Rozengurt, E. (2002) Expression of bitter taste receptors of the T2R family in the gastrointestinal tract and enteroendocrine STC-1 cells. Proc Natl Acad Sci U S A 99, 2392-2397.

EP06826584.2 Search Report mailed Jun. 6, 2011.

* cited by examiner

BILIARY/PANCREATIC SHUNT DEVICE AND METHOD FOR TREATMENT OF METABOLIC AND OTHER DISEASES

RELATED APPLICATIONS

This application is related to and claims priority of U.S. provisional application Ser. No. 60/729,770, filed Oct. 24, 2005, the contents of which are hereby incorporated by reference as if set forth in their entirety.

This application is a national stage application under 35 U.S.C. §371 of International Application No. PCT/US2006/041521, filed 24 Oct. 2006 and which claims priority of U.S. provisional application Ser. No. 60/729,770, filed Oct. 24, 2005, the contents of which are hereby incorporated by reference as if set forth in their entirety.

BACKGROUND

Obesity and diabetes currently account for approximately 300,000 early deaths per year in the U.S., comparable to smoking. Obesity and diabetes have reached epidemic proportions, with high mortality rates and associated economic costs. The current rate of increase of metabolic disease is sufficiently high to be classified by WHO (World Health Organization) as an epidemic, and as such represents the first non-infectious epidemic.

Diet therapy almost always fails as a measure for treating obesity as about 98% of those who achieve weight loss by diet, regain it within 5 years.

There is currently a dearth of approved effective pharmacotherapies. At least nine known therapies for obesity have been approved by the FDA. It is believed that seven of these have been withdrawn from the market due to toxicity or other failure. Sales of the remaining two therapies, orlistat and sibutramine, are low due to low efficacy and unpleasant side effects. The high demand for therapies is however reflected in annual expenditures of $32B in the U.S. alone for over-the-counter therapies, nutritional therapies, and associated "fringe" medicines.

Surgery is currently the most effective therapy for obesity and diabetes. Of approximately 20 different surgeries that have been attempted for the treatment of morbid obesity, 6 remain, the most successful being the Roux-en-Y gastric bypass (RYGBS), with biliopancreatic diversion. The bariatric procedures currently used include Vertical Banded Gastroplasty (VBG); Gastric bypass using the Roux-en-Y anastomosis; Gastric banding; and the Mini gastric bypass. Vertical banded gastroplasty restricts the size of the stomach using a stapling technique. There is no rearrangement of the intestinal anatomy.

Gastric bypass using the Roux-en-Y anastomosis restricts the size of the stomach by stapling shut 90% of the lower stomach. The proximal intestinal anatomy is re-arranged, thereby bypassing the duodenum. Gastric banding involves placing a gastric band around the outside of the stomach. The stomach is not entered.

Mini gastric bypass utilizes a laparoscopic approach in which the stomach is segmented, similar to a traditional gastric bypass. Instead of creating a Roux-en-Y anastomosis, the jejunum is anastomosed in continuity directly to the stomach, similar to a Billroth II procedure. The unique aspect of the procedure is not based on the laparoscopic approach, but rather the type of anastomosis used.

The biliopancreatic bypass procedure ("Scopinaro procedure") consists of subtotal gastrectomy using a long Roux-en-Y procedure to divert the biliopancreatic juices into the distal ileum. The Biliopancreatic bypass with duodenal switch is essentially a variant of the biliopancreatic bypass. Instead of performing a distal gastrectomy, a "sleeve" gastrectomy is performed along the vertical axis of the stomach. The sleeve gastrectomy decreases the volume of the stomach and the parietal cell mass.

In 2003, approximately 140,000 such procedures were performed within the United States, up from 10,000 per year five years earlier. It is unlikely, due to the rate at which new surgeons can be trained and operating rooms made available, that this number could extend beyond approximately 200,000 per year in the near future. At the same time, the number of patients eligible for and in need of such surgery in the United States is at least 12 million, and depending upon criteria established largely by insurers, may be as high as 23 million.

Bariatric surgery is expensive, costing approximately $20,000, and complications requiring surgical correction are approximately 11%. Mortality rate is about 0.5-1.5%. Some patients eligible for bariatric surgery require presurgical weight loss to reduce operative risk and difficulty.

There is therefore an acute need for less expensive interventions, with durable effect, that can be performed faster and with less risk, but that mimic the benefits of bariatric surgery.

There is controversy however, over which aspects of the surgery are responsible for the observed efficacy. Elements of the surgery that are believed to contribute to this efficacy include gastric factors and intestinal factors. Gastric factors include reduced gastric size, increased sensations of gastric distension and reduced production of the orexigenic hormone, ghrelin. Intestinal factors include reduced absorptive area, shunting of unabsorbed calories to distal gut, shunting of bile to distal gut and persistence of digestible luminal signals in distal gut.

Several surgical techniques and devices directed to enhancing or replacing bariatric surgeries have concentrated upon inducing gastric factors that normally result responsive to surgery. Devices and procedures aimed at reducing actual gastric size include the Micropouch procedure as in U.S. Pat. No. 6,758,219, a constrictive coating applied to the outside of the stomach as in U.S. Pat. No. 6,572,627, and the vertical gastroplasty procedure as in U.S. Patent Publication No. 2004/0097989A1. Some devices attempt to bypass the accommodating volume and digestive environment of the stomach by the insertion of a gastric sleeve such as in U.S. Patent Publication No. 2004/0039452A1 and WIPO publication WO/2003086247A1.

Devices and procedures directed to restricting food influx into the stomach include banding devices such as and U.S. Patent Publication No. 2004/0049209A1, U.S. Patent Publication No. 2004/0097989A1, and U.S. Pat. No. 4,592,339 or other restrictors as in WO/2003086246A1. Other devices are directed to creating an artificial distension signal, either by occupying space, as with balloons such as in WO/200235980A3 and WO/2004019765A2 and other intragastric expanders as in U.S. Pat. Nos. 6,675,809 and 5,868,141.

Other approaches that aim to moderate rate of stomach emptying by local treatment of the pylorus, e.g. with pharmacologic agents, appear in U.S. Patent Publication No. 2004/0089313A1. U.S. Patent Publication No. 2004/0015201A1 is directed to moderating rate of stomach emptying with electro stimulation. Other approaches aim to mimic non-gastric aspects that may contribute to effects of RYGBS. These include the inhibition of digestion and absorption. These approaches apply an impermeable barrier between the chyme (undigested food) and the absorptive intestinal wall, for varying lengths of the intestine. In one known application, the barrier is applied as a liquid, or as a film bonded to the gut (see U.S. Pat. No. 4,315,509 and U.S. Patent Publication No. 2003/0191476A1). Sleeves of various configurations have been described in U.S. Pat. Nos. 4,501,264, 5,306,300 and 5,820,584, WO/2003094785A1, and WO/2004049982A2. The sleeves principally vary in their point of origination, some anchored within the stomach, and some distal. WO/03094785A1 provides a sleeve device anchored just below the esophageal sphincter to isolate the stomach as well as continuing as a barrier to absorption within the proximal small bowel.

Another device is based within the pylorus, with a tubular duodenal extension to delay intermixing of digestive enzymes with food exiting the stomach, as in U.S. Pat. No. 5,820,584. A flexible tubular screen has also been designed with a ring that is self-anchoring within the antrum, and a "brush-like" distal end that is subject to normal peristaltic forces to keep it extended within the gut. This device also aims to maintain separation between food and digestive juices and claims advantages over the devices of described in U.S. Pat. No. 4,315,509 to Smit and U.S. Pat. No. 4,501,264 Rockey. The sleeve of Rockey was described to generally isolate any viscera from its detrimental contents, but in the context of obesity, was described only as being placed within the stomach to limit digestive processes therein. Most recently, the bariatric sleeve of Levine et al., WO/2004049982A2 and U.S. Publication No. 2004/0107004 is described as anchored in the stomach. Anchors have also been designed that sit just distal to the pylorus within the duodenum. The intent of such devices is also to separate food from the absorptive duodenum.

The working principles of the above devices are essentially twofold: to restrict meal capacity and/or flow, and/or to apply a barrier to digestion and/or absorption.

Devices currently marketed include banding devices. These have lesser efficacy in the treatment of morbid obesity than does RYGBS, and typically result in loss of approximately 50% of excess body weight. Nonetheless, sales of such a device by one manufacturer (InaMed) are currently approximately $60M per year, indicating that there is a need for such therapy, despite requiring 65-78 minutes of invasive surgery to install the device, an efficacy limited to 38-45% excess weight loss in registration PMA studies, the need to periodically adjust the tightness of the band, and complications in approximately 10% of patients.

As such, there is a demonstrated need and market for improved weight loss devices.

SUMMARY

To address these and other needs and in view of its purposes, the present invention provides, in one aspect, a shunt device comprising a catheter that facilitates transfer of at least one endogenous secretion from the biliary/pancreatic tree of an animal to at least one distal entry location of the gut that is further along the digestive tract than the normal anatomical entry location of the endogenous secretion into the digestive tract. The shunt device may isolate the at least one endogenous secretion from enteroendocrine cells lining the gut until the endogenous secretion reaches the distal entry location.

According to another aspect, provided is a shunt device comprising a conduit that facilitates transfer of at least one endogenous secretion from the biliary/pancreatic tree of an animal to at least one distal entry location of the gut that is further along the digestive tract than the normal anatomical entry location of the endogenous secretion into the digestive tract. The shunt device is endoscopically insertable into a human. The shunt device may isolate the at least one endogenous secretion from enteroendocrine cells lining the gut until the endogenous secretion reaches the distal entry location.

According to another aspect, the invention provides a method for enhancing secretion of gut peptides from enteroendocrine cells lining the gut in an animal by directing bile secreted from the gall bladder or directed through the hepatic duct to at least one distal location further down the digestive tract than the normal anatomical entry point of the bile into the digestive tract, via a catheter, thereby enhancing secretion of gut peptides from enteroendocrine cells lining the gut in an animal.

According to another aspect, the invention provides a method for producing weight loss in an animal. The method includes preventing at least one endogenous secretion from the biliary/pancreatic tree from contacting cell linings in the gut of an animal until the least one endogenous secretion reaches at least one distal location further down the digestive tract than the anatomical entry point of the least one endogenous secretion into the digestive tract, thereby enhancing secretion of gut peptides from enteroeridocrine cells lining the gut in the animal, slowing emptying of the stomach and effecting weight loss in the animal.

BRIEF DESCRIPTION OF THE DRAWING

The present invention is best understood from the following detailed description when read in conjunction with the accompanying drawing. It is emphasized that, according to common practice, the various features of the drawing are not necessarily to scale. On the contrary, the dimensions of the various features may be arbitrarily expanded or reduced for clarity. Like numerals denote like features throughout the specification and drawing.

DETAILED DESCRIPTION

It is an aspect of the present invention to direct the entry of endogenous digestive secretions such as bile, pancreatic juice or a mixture of both to a point more distal in the gut than the normal, anatomical entry point, the Ampulla of Vater, where the common bile duct and therefore the biliary/pancreatic tree, enters the duodenum. This is accomplished through the use of a medical/surgical device. The device may be implanted for acute effect, or it may reside permanently within an individual. The medical device may be a catheter or other conduit that facilitates the transfer of the endogenous digestive secretions from the biliary/pancreatic tree to parts of the gut that are more distal than where they would normally enter. The device isolates the endogenous digestive secretions from enteroendocrine cells lining the gut until the endogenous digestive secretions reach the distal entry location.

Embodiments of the device may include catchment systems to efficiently drain biliary/digestive fluids from their sites of secretion. These systems facilitate desired communication between different parts of the pancreaticobiliary tree without allowing stasis of fluids, and without becoming blocked with stones or particulate matter. Attributes of the catchment system include, without limitation, assisting the drainage from one or more of the gall bladder, the cystic duct, the common bile duct, and the common hepatic duct. Bile and pancreatic flows can be separately collected, kept distinct, and discharged separately, if necessary by the configuration of different conduits and orifices. Other suitable systems assist in the communication between the structures drained such that there is little or no obstruction to flow within any part of the biliary tree. Drainage configurations act to resist blockage through having multiple potential flow paths. Conduits for drainage may include a lumen or multiple lumens within the catheter, grooves or other flow passages on the external surface of the catheter, and holes that communicate between both, as will be shown. The external grooves may form an interconnecting net. According to the exemplary embodiment in which several lumens are provided, the obstruction of a single lumen does not preclude distal delivery. There may be several communications between external grooves and an internal lumen. The ordering of diameters of consecutive conduits in flow paths resists blockage, for example by a progressive increase in diameter in the direction of flow.

Figure 1:
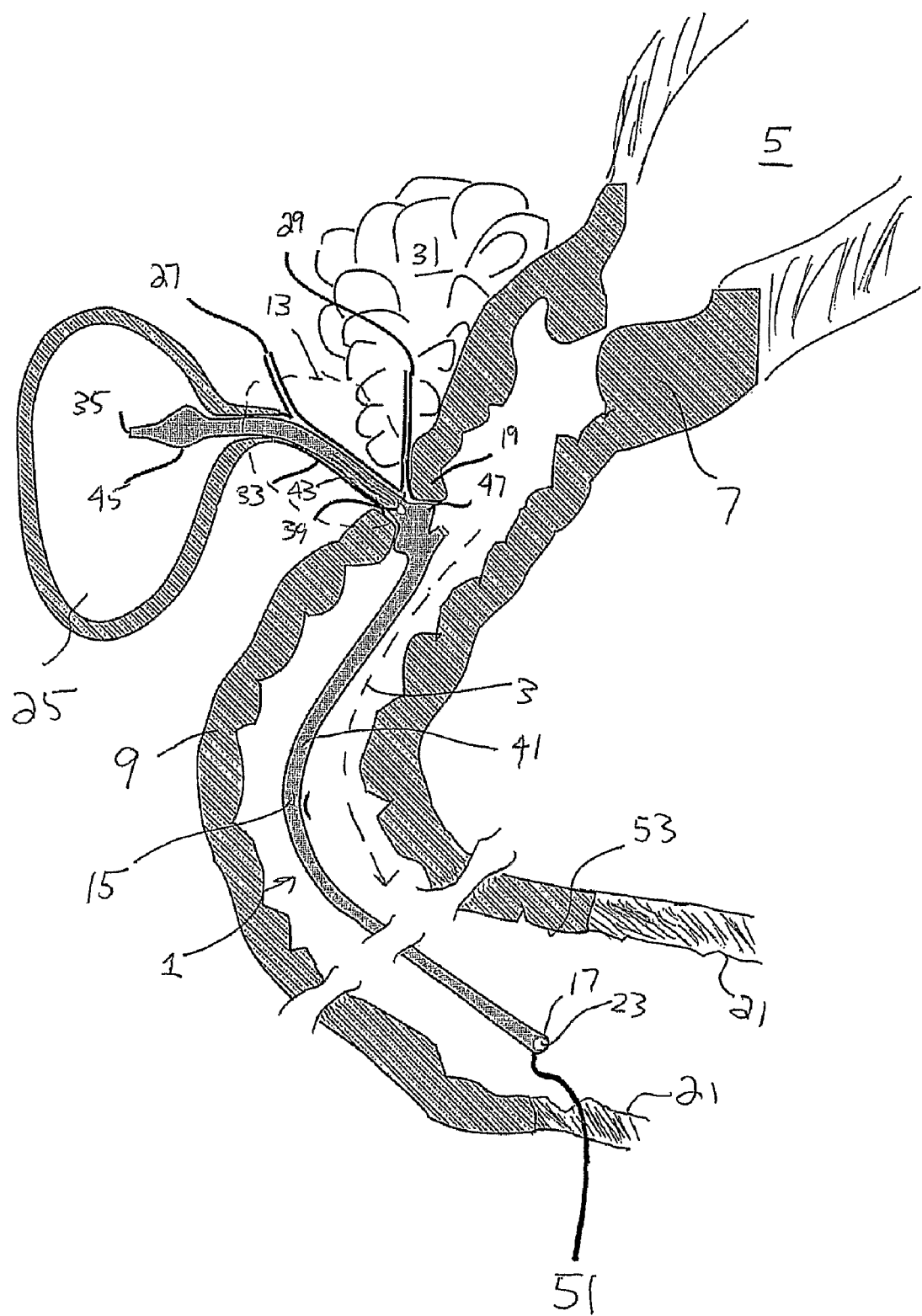
FIG. 1 is an internal perspective view in partial cross-section illustrating an exemplary shunt device according to the invention.

FIG. 1 is a diagram of an exemplary shunt device according to the invention. In the illustrated embodiment, the shunt device capable of shunting digestive secretions is a flexible catheter, generally impervious to such secretions and which may be inserted into the common bile duct using surgical or non-surgical procedures such as endoscopy. Shunt device 1 extends along digestive tract 3 of a human or other animal. Digestive tract 3 includes antrum 5 of the stomach, and extends past duodenal cap 7 and into duodenum 9 and may extend into the jejunum, the ileum and the colon as will be shown in FIG. 2. Shunt device 1 which extends along digestive tract 3 is in the form of a catheter in the illustrated embodiment but other suitable conduits may be used in other exemplary embodiments.

Shunt device 1 transports endogenous digestive secretions from biliary/pancreatic tree 13 to locations along the digestive tract 3 such as exemplary exit ports 15 and 17 (the terminal exit port) each of which are further down the digestive tract than the anatomical or normal entry location at which the secretions would enter the digestive tract, i.e., at the Ampulla of Vater 19 in duodenum 9. In one embodiment, the endogenous secretions from biliary/pancreatic tree 13 are isolated from enteroendocrine cells along lining 21 of lumen 53 of the gut until they are transferred to the exit port or ports. In this manner, endogenous digestive secretions such as bile reach locations further down digestive tract 3 than they normally would and the interaction between such endogenous digestive secretions and the enteroendocrine cells that line lumen 53 further down the gut, cause enhanced secretion of several potentially therapeutic gut peptides from the enteroendocrine cells as will be discussed below.

Shunt device 1 may be formed of Teflon or other suitable materials that are impervious to chyme, the endogenous digestive secretions and other physiological fluids. In the illustrated embodiment, the catheter includes one lumen 23 but in other exemplary embodiments, the catheter may include multiple lumens. Endogenous secretions may emanate from gallbladder 25, and/or the liver via hepatic duct 27 and/or duct 29 of pancreas 31. In the illustrated embodiment, shunt device 1 extends through common bile duct 33. In the illustrated embodiment, bile from gallbladder 25 and hepatic duct 27 are transferred to an entry point in the digestive tract that is further along than the anatomical, normal entry point being the Ampulla of Vater 19 of duodenum 9, but pancreatic fluid from duct 29 is allowed to enter the digestive tract 3 at Ampulla of Vater 19. In other exemplary embodiments, each of the fluids may be transported to digestive tract 3 at an entry location further along digestive tract 3 than Anpulla of Vater 19.

Bile drainage from gall bladder 25 can be into one or more orifices that communicate with the proximal end of the catheter. Originating entry port 35 within gallbladder 25 receives bile from gallbladder 25 in the illustrated embodiment. Bile from hepatic duct 27 is directed into shunt device 1 via entry port 39 which is an orifice extending through wall 41 of the catheter, which may include a thickness of 0.1 to 1.5 mm in one exemplary embodiment, but other suitable thicknesses may be used in other exemplary embodiments. Channels or grooves 43 are formed along wall 41 of shunt device 1 in common bile duct 33 and, in this location, a stent or other expansile device may be used to apply radially outward pressure to the catheter within bile duct 33 urging walls 41 of the catheter to maintain a conterminous relationship with internal surfaces of bile duct 33. In this manner, bile from hepatic duct 27 is directed along grooves 43 and into entry port 39. In contrast, enzyme-containing soluble pancreatic fluid that enters the digestive system via duct 29 and pancreas 31, remains external to the catheter and enters digestive tract 3 at Ampulla of Vater 19. Other arrangements may be used in other exemplary embodiments.

In various exemplary embodiments, shunt device 1 has a fixation or stabilization system to stabilize the device and position it such that it is maintained stable relative to associated anatomical structures, and is not passed or regurgitated. Any suitable stabilization system used in medical procedures, including those later developed, may be used. One suitable fixation systems includes balloons.

In some exemplary embodiments, balloons that expand to a diameter greater than that of a duct in which another part of the catheter resides, are utilized. The bulk portion of the catheter may include a diameter ranging from 3 mm to 20 mm but other diameters may be used in other exemplary embodiments. This fixation device thereby inhibits movement of the catheter in either direction such as in the illustrated embodiment, in which the portion of shunt device 1 within bile duct 33 is maintained in fixed position through the use of balloons 45 and 47 which serve as anchoring members or anchoring cuffs located at the throat of gallbladder 25 and within the gut lumen, to prevent further ingress. The diameter of the catheter is increased relative to the base diameter of the catheter at balloons 45 and 47. One or more of the exemplary balloons may, for example, be inflated with liquid or gas after insertion. The exemplary balloons may alternatively be preinflated with a compressible fluid, or with a fluid that, for example, is connected with another reservoir so that the balloons may be reduced during insertion, or the balloons may be preinflated with a non-compressible fluid that allows both passage through a duct during insertion, but fixation when in situ. Balloons 45 and 47 may also be formed of a solid material, functioning in a similar way to a non-compressible liquid. Balloon expansions may occur around parts of the device within the gall bladder, or within the gut lumen, for example, or within other such compliant parts of the biliary tract. Balloons 45 and 47 provide the advantage of a reduced source of inflammation at point of immobilization compared to device anchors that require sutures or penetrating barbs which increase the potential of perforation or infection, given sufficient opportunity.

In other exemplary embodiments, other fixation means may be used to fixedly position shunt device 1 within the animal's anatomy. Stents or other expansile components are used such that the device appose the interior of a duct and thereby maintain a fixed relationship with the anatomy. These may include components that are expanded with balloons or other specialized tools. Expansile components may include "memory metals" such as nitinol which change shape in a temperature dependent manner. Expansile anchoring systems may also be spring-loaded. The relationship with the apposing tissue may be friction. The anchoring system may include prongs, barbs or other elements that penetrate the tissue surface, or otherwise augment frictive properties. Some embodiments of the device include adhesives either delivered separately, or incorporated into the device. In other exemplary embodiments, still other suitable anchoring members may be used.

Embodiments of shunt device 1 may incorporate a deployment/extension system to promote the intraluminal positioning of shunt device 1 in an anatomical relationship in which it adequately functions, and prevents undue coiling of shunt device 1, formation of knots, or any tendency of the device to promote bowel obstruction, injury or other complications. Any suitable deployment/extension system known in the art or later developed may be used. Suitable deployment/extension systems include, but are not limited to a tail or area of bulk that promotes peristaltic or bulk-flow passage of the free end of the device to distal parts of the gut.

In another exemplary embodiment, shunt device 1 may include an incorporated weight, or gravimetrically dense part of the device, that promotes delivery, positioning and residence of that part in more dependent, i.e. distal parts of the gut. Shunt device 1 may include means for stiffening the catheter. Stiffening of the device may be accomplished by any suitable approach known in the art or later developed, including incorporating into the walls of the device ribs, wires or other stiffening or semi-rigid materials that minimize coiling, kinking, or formation of knots or other obstructions.

The catheter of shunt device 1 is flexible and impervious to bile/pancreatic fluid, other endogenous secretions, chyme and other digestive secretions. One aspect of shunt device 1 is that the material of external surface of walls 41 is selected to minimize adherence to bowel. The internal surfaces of shunt device 1 are typically selected to minimize aggregation of particulate matter and will especially minimize colonization by bacteria.

Another aspect of shunt device 1 is that it is formed to include a flexibility that is sufficient to allow compliance with normal motion of the bowel, while being sufficiently stiff to inhibit coiling. Elasticity is chosen to be sufficient to allow requisite flexibility, but not such to promote pinching or entanglement of tissue. Shunt device 1 is formed of material that is strong and durable and sufficient to ensure integrity on insertion and removal, and to resist breakage under constant flex. Various materials such as Teflon or other polymers, may be used to form shunt device 1 and it is contemplated that embodiments of shunt device 1 may incorporate material and engineering improvements made in the future. Materials research and development, systems for manufacture, and clinical application for catheters is advancing rapidly, and various suitable new materials that may be used for shunt device 1 and expected to be available in the near future.

Shunt device 1 is designed to desired structural and physical properties. Shunt device may remain in situ for months or longer for certain applications. In such embodiments, shunt device 1 will advantageously include certain attributes. For example, shunt device 1 may be advantageously made using biocompatible materials that will not be toxic or cause chemical irritation.

In another aspect, shunt device 1, impervious to bile and other physiologic fluids, is formed of materials not be affected by large changes in pH or other features of the fluids which it will contain or contact.

Terminal end 51 is left to trail within lumen 53 of the gut and is eventually propelled caudally by normal peristaltic movements of the gut. According to the embodiment in which shunt device 1 includes multiple lumens instead of just the single illustrated lumen 23, different endogenous digestive secretions may be maintained separate from one another. For example, it may be desired to keep pancreatic fluid 13 and bile in separate lumens and to be introduced into digestive tract 3 at different locations. For example, pancreatic fluid from duct 29 may enter the catheter at an entry port situated at duct 29, extend through a first lumen of the catheter and exit at a first exit port such as exit port 15 while at the same time bile from gallbladder 25 enters the catheter at originating entry port 35 and extends through a further lumen of the catheter to terminal exit port 17. The lumens may include inner diameters within the range of about 2 mm to about 30 mm. According to one embodiment of the device, the different exit locations may be different levels of the gut distributed between the jejunum and colon. Determinants of the distribution of site of exit will include greatest aggregate efficacy of the device, least incidence and severity of side effects, least hazard, and factors related to manufacture and placement. In other exemplary embodiments, other arrangements may be used. In another exemplary embodiment, pancreatic fluid and bile may be mixed within the catheter. Generally speaking, shunt device 1 may be configured to direct secreted body fluids such as bile and pancreatic juice to various desired sites of delivery.

Exemplary sites of delivery (shown in FIG. 2) include, without limitation, those proximal-, mid-, and distal-jejunum, proximal-, mid-, and distalileum, cecum, ascending-, transverse- or descending colon. A preferred site of delivery is the ileum. The device may include, one or several exit ports that deliver flow to more than one of the locations listed. In certain embodiments, the port diameter and other determinants of hydraulic resistance are controlled to partition flow to different gut segments in order to optimize a balance between efficacy, side effects and hazard.

According to another exemplary embodiment, some portion of the flow may be delivered to the normal anatomical location in an unobstructed manner to allow substantially normal digestion and absorption of nutrients, vitamins and other components of the meal, and to allow, for example, generation of normal products of digestion which may in themselves promote enteroendocrine secretion. For example, some of the bile may be allowed to enter the digestive tract at Ampulla of Vater 19.

Figure 2:
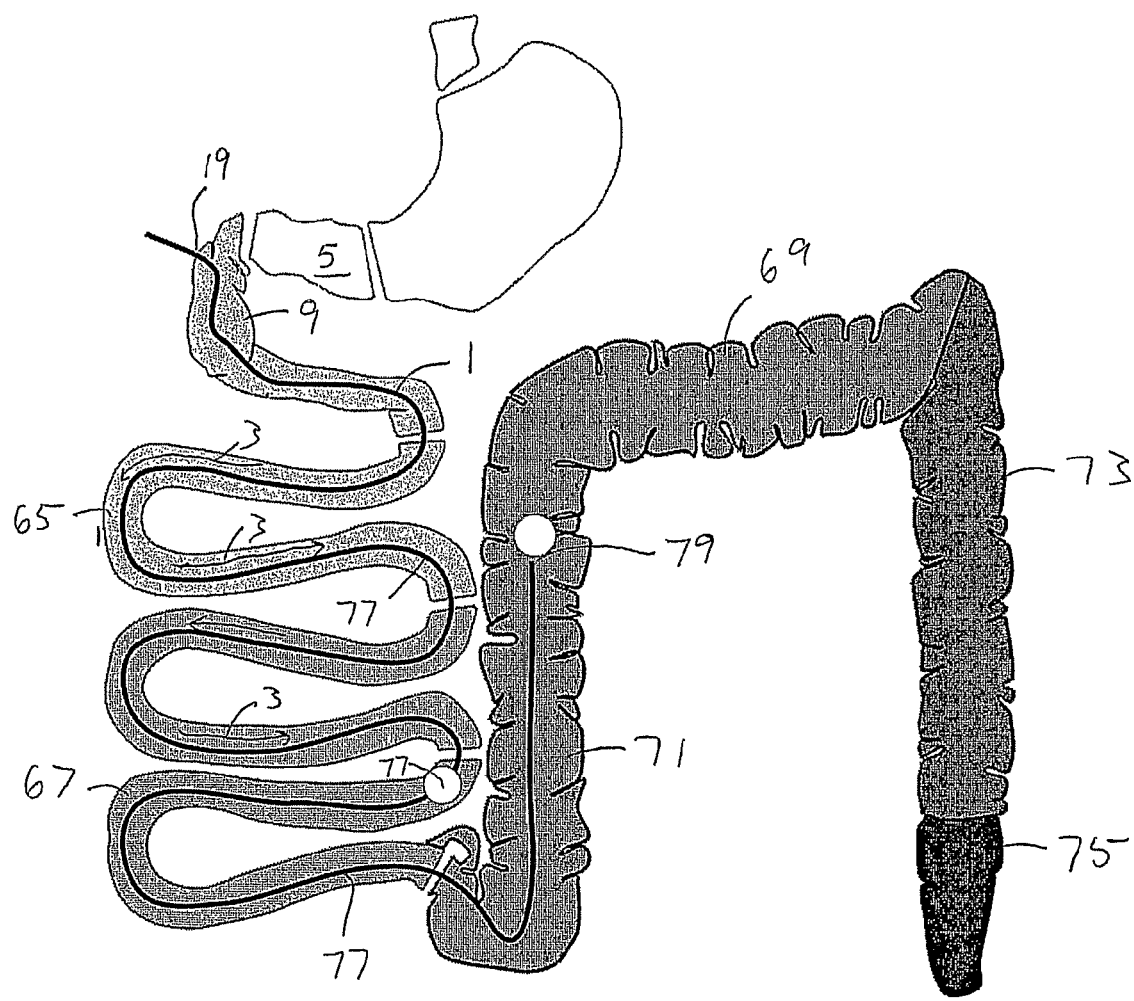
FIG. 2 is an illustration of a human digestive tract showing exit ports of the exemplary shunt device.

FIG. 2 shows relevant portions of a human's digestive system including antrum 5 of the stomach, duodenum 9, jejunum 65, ileum 67, colon 69 including ascending colon 71 and sigmoid colon 73, and rectum 75. Shunt device 1 extends along digestive tract 3 entering the gut lumen at normal anatomical entry point, Ampulla of Vater 19 in duodenum 9 located at biliary/pancreatic tree 13. Shunt device 1 may include one or a plurality of exit ports that may have different diameters to accommodate different volumes of the endogenous secretion to exit the catheter at different locations. Locations 77 may represent exit ports at locations described above but are intended to be exemplary only and the exit ports may be located at various locations in other exemplary embodiments. The terminal exit port located at terminal end 79 may be at various locations, i.e., shunt device 1 may extend to various lengths along digestive tract 3.

The length of shunt device 1 may be tailored to a particular patient. The length of the device will be sufficient to allow delivery to locations stated above. The average length of the small intestine in the adult human male is 6.8 meters (7.1 meters in the female), with extremes of 9.7 and 4.7 meters in certain individuals. The length of the bowel is independent of age, height, and weight. The length of shunt device 10 may range from 0.5 and 10 meters, preferably between 1 and 6 meters, most preferred around 3 meters, but such lengths are exemplary only.

Figure 3A:
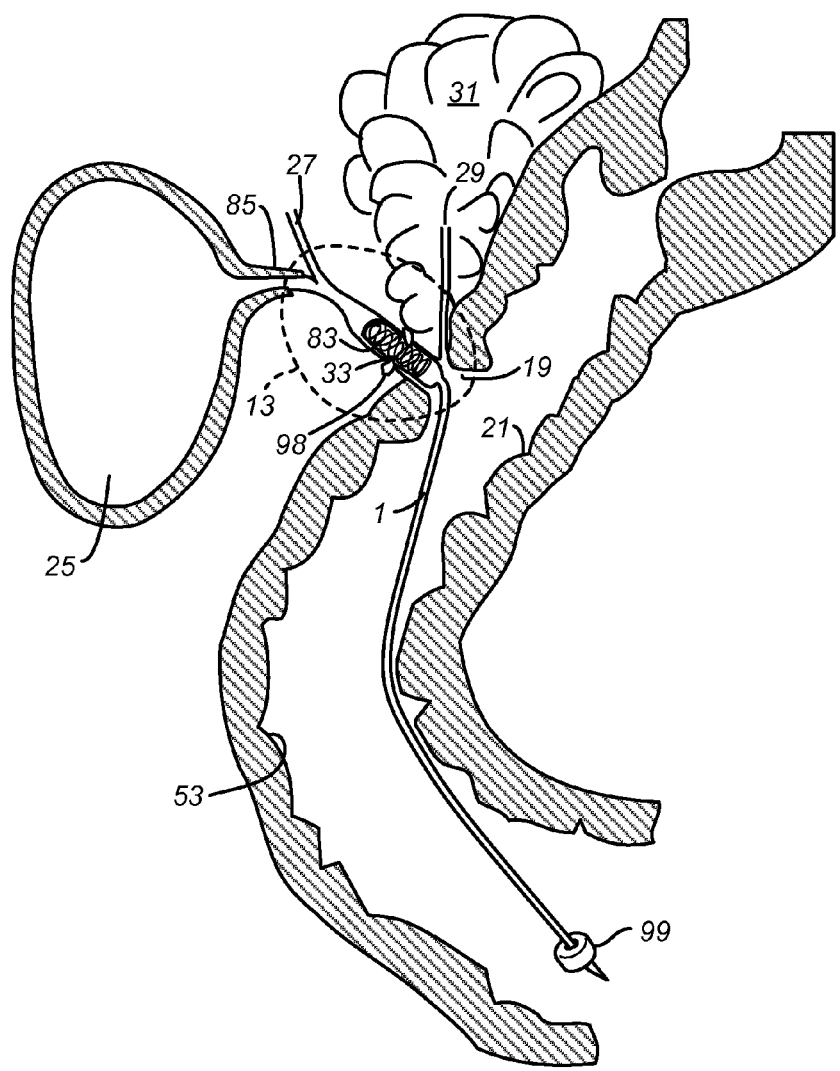
FIG. 3 is an internal perspective view in partial cross-section illustrating another exemplary shunt device according to the invention.
Figure 3B:
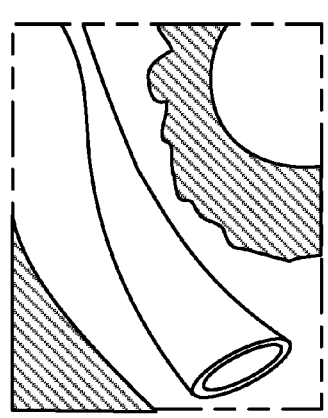

FIG. 3A shows another exemplary embodiment of the shunt device 1 of the invention. According to this exemplary embodiment, originating entry port 81 is located within common bile duct 33. According to this exemplary embodiment, the catheter includes a catchment device that enables both bile from gallbladder 25 and hepatic duct 27 to enter shunt device 1 at originating entry port 81. Stent 83, optionally having barbs or prongs 98, is disposed within shunt device 1 in common bile duct 33 and applies radically outward pressure to force walls 41 of the catheter against the inner walls of common bile duct 33 therefore accommodating the entry of bile from both locations. Shunt device 1 does not reside within cystic duct 85 in this exemplary embodiment. According to the exemplary embodiment illustrated in FIG. 3A, the pancreatic fluid enters gut lumen 53 and along digestive tract 3 at its normal anatomical location, Ampulla of Vater 19. In another exemplary embodiment, shunt device 1 may include an incorporated weight or gavimetrically dense portion 99, that promotes delivery, positioning and residence of that part in more distal parts of the gut. FIG. 3B shows another exemplary embodiment, wherein the ordering of diameters of consecutive conduits in flow paths resists blockage, for example by a progressive increase in diameter in the direction of flow.

The shunt device 1 and method of treatment according to the invention provides numerous advantages over previous devices and methods, including, for example, a reduced tendency to promote bowel obstruction. Anchored devices, especially those where the anchor is non-compressible, may cause obstruction if the anchor comes loose. Sleeve devices have a theoretic risk of obstruction due to kinks and knots in the sleeves which are universally flaccid, without inherent tendency to remain open or unknotted. The shunt device of the invention is small having an outer diameter ranging from 3 mm to 20 mm, will unlikely obstruct if it comes loose, and can be configured sufficiently stiff to not coil or knot.

According to another aspect, shunt device 1 may be custom configured to accommodate the needs of a particular patient. For example, one of the configurations, will accommodate the significant proportion of patients who have had a cholecystectomy, and will not have elements designed to reside within the gall bladder. Configurations will also accommodate patients who have the more common natural variations in biliary tract anatomy.

The device is also advantageous in that it includes simple insertion and removal procedures. Many endoscopists are already familiar with cannulation of the bile duct for endoscopic removal of gall stones by endoscopic retrograde cholangiopancreatography (ERCP), and already possess the tools necessary for the procedure. In contrast to special sleeve devices and others, few if any specialist tools are necessary.

According to one exemplary embodiment, the materials utilized in the device may, for example, be radio-opaque, including having distinctive markers at certain places on the device, to assist with placement, assessment of position and function, and with other aspects of clinical management. Other contrasting techniques may also be used to visualize placement, including ultrasound contrasting and MRI contrasting.

The effect of the device is to effectuate enhanced secretion of several potentially therapeutic gut peptides from enteroendocrine cells lining the gut of humans or other animals although the effect of the device is not limited to such mechanism. Therapeutic effects of such stimulation will be manifest in a range of metabolic, cardiovascular, digestive and other diseases. Stimulation of enteroendocrine secretions typically results from detection of both nutrient and non-nutrient stimuli in the gut lumen.

In one exemplary embodiment, shunt device 1 may be employed to facilitate the efficient anterograde drainage of the pancreatic duct (which drains into the common bile duct in 95% of individuals) as necessary to prevent pancreatitis. Efficient drainage of the biliary tree is necessary to prevent cholangitis, bile stasis and cholelithiasis.

Another exemplary mechanism is discussed below. Under normal metabolic conditions, bile and nutrient macromolecules do not reach distal portions of the gut as they are mixed beginning at the anatomical entry port, the Ampulla of Vater at which point the bile begins assisting the breakdown of the nutrient macromolecules into peptides, sugars and individual fatty acid molecules. When the large nutrient macromolecules reach distal portions of the gut lumen, i.e., points further along the digestive tract than their normal entry point, they stimulate enhanced enteroendocrine secretions. The presence of unabsorbed bile at this distal location also stimulates enhanced enteroendocrine secretions as it sends a signal that chyme is moving too quickly throughout the digestive system. The enteroendocrine secretions effectuate satiety. The reflexive reaction is to slow stomach emptying, in effect tricking the body into thinking that too much chyme is passing through the digestive system too quickly. Such effects lead to weight loss and reduced obesity. Without being limited to the following mechanisms, the effect of the device and method of the invention is as follows.

The gastrointestinal tract senses diverse meal-related stimuli, and secretes a number of peptides and proteins (both exocrine and endocrine) in response to meals. At the stomach, gastrin is secreted in response to calcium, amino acids and fermented glucose. Gastric inhibitory polypeptide (GIP), secretin and cholecystokinin (CCK) are secreted in response to fat; CCK and GIP in response to duodenal glucose; and GIP and CCK in response to certain amino acids, although other metabolic responses may occur as well. Responses to protein meals depend upon their breakdown to amino acids. Neurotensin and glucagon-like peptide-1 (GLP)-1 are secreted in response to fat and carbohydrate in the ileum. Specific mechanisms sensing these nutrient signals are not fully characterized, but can include receptors on apical microvilli of endocrine cells or indirect sensing via the intrinsic nervous system and/or accessory cells.

A long-recognized example of nutrient sensation in the gut is exemplified in its ability to respond to fat. For example, long chain fats (C12 or greater), drive CCK stimulation within minutes of application but reportedly only when chylomicron formation is enabled. The involvement of sensorineural structures in gastrointestinal responses to fat stimuli is suggested by their blunting when afferents are destroyed by local application of capsaicin neurotoxin (see Lloyd, K. C., Holzer, H. H., Zittel, T. T. and Raybould, H. E. (1993) *Duodenal lipid inhibits gastric acid secretion by vagal, capsaicin-sensitive afferent pathways in rats*, Am J Physiol 264, G659-G663). GLP 1 is also secreted in response to fat, but apparently depends on at least partial digestion, since responses are blunted when a lipase inhibitor is added as discussed in Pilichiewicz, A., O'Donovan, D., Feinle, C., Lei, Y., Wishart, J. M., Bryant, L., Meyer, J. H., Horowitz, M. and Jones, K. L. (2003) *Effect of lipase inhibition on gastric emptying of, and the glycemic and incretin responses to, an oil/aqueous drink in type 2 diabetes mellitus*, J Clin Endocrinol Metab 88, 3829-3834. Chemosensory mechanisms within the gut are not fully understood but can include the same receptors responsible for taste at the tongue as reported in Wu, S. V., Rozengurt, N., Yang, M., Young, S. H., Sinnett-Smith, J. and Rozengurt, E. (2002) *Expression of bitter taste receptors of the T2R family in the gastrointestinal tract and enteroendocrine STC-1 cells*, Proc Natl Acad Sci USA 99, 2392-2397.

Gut peptides that are secreted in response to intraluminal meal-related stimuli such as delivered to distal locations of the gut according to the shunt device and method of the invention, are shown in Table 1. Several, such as CCK, GLP-1, PYY, oxyntomodulin and neurotensin inhibit feeding, and through this and/or other mechanisms, can induce weight loss.

TABLE 1

| Peptide | Luminal Secretagogue | Cells of Origin |
| --- | --- | --- |
| Gastrin | Esp. aromatic amino acids and amines | G cells |
| Somatostatin | Intragastric acid | D cells |
| Secretin | Intraduodenal acid | S cells |
| CCK | Fats, proteins | I cells |
| GIP | Carbohydrates, triglycerides | K cells |
| Motilin | Poss. duodenal alkaline | M cells |
| GLP-1, -2 | Carbohydrates (incl. non-metabolized) | L cells |
| Pancreatic Polypeptide (PP) | Vagal, intraluminal amino acids, glucose, fat | PP cells |
| Peptide YY | Intraluminal fat, protein | L cells |
| Oxyntomodulin | Intraluminal fat | L cells |
| Neurotensin | Jejunal fat | N cells |

The site of release of such gut peptides is variable. Their distribution throughout the gut is not typically uniform, as indicated in Adrian, T. E., Bacarese-Hamilton, A. J., Smith, H. A., Chohan, P., Manolas, K. J. and Bloom, S. R. (1987) *Distribution and postprandial release of porcine peptide YY*, J Endocrinol 113, 11-14 which provides the exemplary gut concentrations of peptide YY (PYY) being: antrum<1, duodenum 5.7+/−0.9; jejunum 4.7+/−1.0; ileum 84+/−8; ascending colon 82+/−9; sigmoid colon 196+/−34; and rectum 480+/−66. This distribution is reported to be similar in humans and pigs.

Tissue concentrations of PYY, for example, increases with progression down the gut. Similarly, in another study, a continuous increase in cells positive for GLP-1 (partly co-localized with PYY) was evident from the proximal to the distal portion of small and large bowel. (Eissele, R., Goke, R., Willemer, S., Harthus, H. P., Vermeer, H., Arnold, R. and Goke, B. (1992) *Glucagon-like peptide-1 cells in the gastrointestinal tract and pancreas of rat, pig and man*, Eur J Clin Invest 22, 283-91). The site of release is not necessarily predicted by tissue content; for example, even though tissue content continuously increases with progression along the gut, most release of GLP-1 is considered to come from the terminal ileum, by which segment most of the nutrient is previously absorbed without the shunt device of the invention. The presence of gut peptides beyond that level may represent a "fail-safe" in that, with progression down the gut, increasingly vigorous secretion occurs in the decreasingly probable event that nutrient or other secretagogues reach therein unaltered animals. The method and device of the invention delivers such nutrients and secretagogues to such locations down the gut.

Non-nutrient Endogenous Stimuli.

Evidence indicates that quasi-endocrine systems exist in the gut, whereby secreted signals traverse the gut lumen and act upon receptors in the gut wall. One example is luminal CCK-releasing factor (LCRF).

Luminal CCK Releasing Factor.

A 41 amino acid factor present in secretory cells distributed throughout the length of the gut (Spannagel, A. W., Green, G. M., Guan, D., Liddle, R. A., Faull, K. and Reeve, J. R. Jr (1996) *Purification and characterization of a luminal cholecystokinin-releasing factor from rat intestinal secretion*, Proc Natl Acad Sci USA 93, 4415-4420), but especially concentrated in the small intestine, was found to stimulate pancreatic secretion in vivo via release of CCK (Spannagel, A. W., Reeve, J. R. Jr, Liddle, R. A., Guan, D. and Green, G. M. (1997) *An amino-terminal fragment of LCRF, LCRF-(1-35), has the same activity as the natural peptide*, Am J Physiol 273, G754-G758). This stimulation of CCK secretion occurred with dispersed intestinal mucosal cells and on STC-1 cells (Wang, Y., Prpic, V., Green, G. M., Reeve, J. R. Jr and Liddle, R. A. (2002) *Luminal CCK-releasing factor stimulates CCK release from human intestinal endocrine and STC-1 cells*, Am J Physiol Gastrointest Liver Physiol 282, G16-G22) and suggests a direct effect of the factor (termed Luminal CK-releasing factor; LCRF). Shorter fragments of LCRF (1-35), (11-25) were less potent, and (1-6) was totally ineffective in stimulating secretion (Spannagel, A. W., Reeve, J. R. Jr, Greeley, G. H. Jr, Yanaihara, N., Liddle, R. A. and Green, G. M. (1998) *Bioactivity of intraduodenally and intravenously infused fragments of luminal cholecystokinin releasing factor (LCRF)*, Regul Pept 73, 161-164). The proposed physiologic role of LCRF is feedback control of intraluminal pancreatic protease activity (Tarasova, N., Spannagel, A. W., Green, G. M., Gomez, G., Reed, J. T., Thompson, J. C., Hellmich, M. R., Reeve, J. R. Jr, Liddle, R. A. and Greeley, G. H. Jr (1997) *Distribution and localization of a novel cholecystokinin-releasing factor in the rat gastrointestinal tract*, Endocrinology 138, 5550-5554). The presence of undigested LCRF is a signal that intraluminal protease activity is insufficient, and it thus stimulates (via CCK) further protease release, digesting the LCRF(1-41) until protease-releasing activity is no longer present. A consequence of shunting pancreatic exocrine secretion to more distal gut segments is that more undigested LCRF will survive passage to its putative receptors within the gut lumen, and thereby amplify CCK release. Countering this mechanism will be delayed access of triglyceride to pancreatic lipase, slowing the generation of fat digestion products that appear necessary for a full CCK response (Pilichiewicz et al. 2003).

Bile Salts

Bile salts are synthesized in the liver and secreted into the intestinal lumen, especially in response to fat-evoked CCK-mediated gallbladder contraction. They assist in fat digestion by micelle formation, a process that emulsifies fat and thereby increases the surface area upon which lipase and other digestive processes may act. The intraluminal bile salt concentration is approximately 10 mM in the upper small bowel, and can increase to 20 mM or more with fluid shifts associated with absorption. To conserve bile salts and minimize the need for synthesis de novo, there is an active recuperative mechanism, the apical sodium-dependent bile salt transporter (ASBT) that pumps free bile salts out of the gut lumen. These are particularly located in the terminal small bowel. Recuperation of bile salts from the gut, return via the portal vein to the liver where the ASBT scavenger is also found and re-secretion back into the bile and gut and is termed the enterohepatic circulation. In addition to the apical sodium-dependent bile salt transporter (ASBT, SLC10A2) in cholangiocytes and enterocytes, major transport proteins involved in the enterohepatic circulation of bile salts include the hepatocellular bile salt export pump (BSEP, ABCB11), the sodium-dependent hepatocyte bile salt uptake system NTCP (SLC10A1), the organic anion transporting polypeptides OATP-C (SLC21A6), OATP8 (SLC21A8) and OATP-A (SLC21A3), and the multidrug resistance protein MRP3 (ABCC3).

Physiologic Rationale for L-Cell Bile Salt Sensitivity.

Downstream of the recuperative region of the gut, intraluminal bile salt concentrations have typically been reduced to 2-3 mM. Excessive bile salts downstream of this region may be regarded as a signal that chyme flow is exceeding recuperative capacity, just as nutrient downstream of this region may also be regarded as a signal that absorptive capacity was being exceeded. The invention permits such signals to acutely infer that food ingestion should decrease, that slowing of gastric emptying was required, more digestive capacity was required, or chronically, that more absorptive capacity was required.

The L-cells secrete peptide hormones (GLP-1, GLP-2, oxyntomodulin and PYY) that accomplish several of the needed responses, may participate in bile salt-mediated feedback control. Bile salts themselves promote secretion of GLP-1 (Plaisancie, P., Dumoulin, V., Chayvialle, J. A. and Cuber, J. C. (1995) *Luminal glucagon-like peptide-1 (7-36) amide-releasing factors in the isolated vascularly perfused rat colon*, J Endocrinol 145, 521-526) and PYY (Plaisancie, P., Dumoulin, V., Chayvialle, J. A. and Cuber, J. C. (1996) *Luminal peptide YY-releasing factors in the isolated vascularly perfused rat colon*, J Endocrinol 151, 421-9) from isolated perfused colon preparations. Perfusion of colon in situ with bile salts also promotes the secretion of GLP-1 and PYY (Adrian, T. E., Ballantyne, G. H., Longo, W. E., Bilchik, A. J., Graham, S., Basson, M. D., Tiemey, R. P. and Modlin, I. M. (1993) *Deoxycholate is an important releaser of peptide YY and enteroglucagon from the human colon*, Gut 34, 1219-1224; Izukura, M., Hashimoto, T., Gomez, G., Uchida, T., Greeley, G. H. Jr and Thompson, J. C. (1991) *Intracolonic infusion of bile salt stimulates release of peptide YY and inhibits cholecystokinin-stimulated pancreatic exocrine secretion in conscious dogs*, Pancreas 6, 427-32). Applicant has found that bile salts may be not only emulsifying agents (detergents), but also serve as monitor signals participating in the distributed control of digestive function. Without limitation, it is in harnessing bile salts to mimic signals of digestive overload that the method and device of the invention is directed to provoking therapeutically useful secretory responses.

The sensitivity of the ileum and other distal gut segments to undigested nutrients such as provided by the shunt device and method of the invention, is considered the origin of signals that reflexly slow gastric emptying, the so-called "ileal brake" concept. Some of the benefits of bariatric surgery may derive from the shunting of undigested nutrients to sensitive gut segments. A consequence of bariatric surgery may also be to shunt non-nutritive signals, such as conveyed with bile, to receptive L-cells and other cells, resulting in gut hormone secretion.

Enhanced secretions of gut peptides including at least one secretory product of an L-cell will be useful for treatment or prevention of: diabetes, impaired glucose tolerance, glucose metabolic disorders, insulin resistance, obesity, acute coronary syndrome, hibernating myocardium, ventricular dysfunction, cardiac risk, post myocardial infarction mortality, post-surgical or sepsis-related or critical illness-related catabolism and mortality, critical illness polyneuropathy, congestive heart failure, toxic hypervolemia, renal failure, ischemia-reperfusion injury, mortality and morbidity from stroke and neurodegenerative disease, neuropathy, inflammatory bowel disease, bowel mucosal injury, impaired bowel integrity, irritable bowel syndrome, osteopenia, and bone fractures and bone disorders. The effect of the device and method of the invention is not, however, intended to be limited to the aforedescribed therapies, nor the disclosed mechanisms.

Several molecular possibilities exist that could underlie sensitivity of enteroendocrine cells to bile salts. Firstly, it may be significant that the T2R bitter taste chemosensory receptor is found in the gut, and that the STC-1 cell line, a model of enteroendocrine L-cell, expresses it and exhibits a secretory signature in response to denatonium, a bitter tastant (Wu et al. 2002). It is proposed that this bitter receptor could partly underlie L-cell sensitivity to bile salts, which are characteristically bitter. Secondly, there is a nuclear receptor, the framesoid X receptor (Chen, F., Ma, L., Dawson, P. A., Sinal, C. J., Sehayek, E., Gonzalez, F. J., Breslow, J., Ananthanarayanan, M. and Shneider, B. L. (2003) *Liver receptor homologue-1 mediates species- and cell line-specific bile acid-dependent negative feedback regulation of the apical sodium-dependent bile acid transporter*, J Biol Chem 278, 19909-19916), that responds to bile acids, and have been proposed to mediate more slow responses, such as induction of various transport proteins. Finally, orphan GPCR's have recently been identified that respond to bile acids. The receptor TGR5, reportedly identified at Takeda (Kawamata, Y., Fujii, R., Hosoya, M., Harada, M., Yoshida, H., Miwa, M., Fukusumi, S., Habata, Y., Itoh, T., Shintani, Y., Hinuma, S., Fujisawa, Y. and Fujino, M. (2003) *A G protein-coupled receptor responsive to bile acids*, J Biol Chem 278, 9435-9440) responded to lithocholic acid and conjugates. The authors in Kawamata et al. proposed an immunosuppressive function and have claimed this receptor in EP application EP 01273659A1 as a screening tool, and claim ligands identified thereby. In claims 30-36 of EP 01273659A1 utility in central dysfunction, inflammatory diseases, circulatory diseases, cancer or diabetes is asserted.

Maruyama, T., Miyamoto, Y., Nakamura, T., Tamai, Y., Okada, H., Sugiyama, E., Nakamura, T., Itadani, H. and Tanaka, K. (2002) *Identification of membrane-type receptor for bile acids (M-BAR)*, Biochem Biophys Res Commun 298, 714-719 from the Tsukuba Research Laboratories (Banyu Pharmaceuticals) report having identified a receptor BG37 that is responsive to bile acids (especially lithocholic) (Maruyama et al. 2002) and that this receptor activates several transduction pathways, including cAMP. The receptor is found throughout most of the gut although not the esophagus or rectum, and in the liver and many other tissues. Its presence in the NCI-H716, STC-1 and GLUTag enteroendocrine cell models was noted. The authors surmised that such a receptor would mediate secretion of GLP-1 and CCK, release of which are associated with cAMP modulation. The method and shunt device of the invention may be used to deliver bile acids to such receptors. European application EP 01347052A1 discloses use of the receptor as a screening tool to identify ligands, including those with sterol and bile acid backbones. Such ligands were contemplated to have potential utility in diseases of heart, lung, muscle, spleen, intestine, liver, kidney and blood.

Biliary Shunting

Meyer U.S. Pat. No. 5,322,697, as part of a proof of concept that undigested fat in terminal small bowel was responsible for weight loss, developed a switchable biliary fistula wherein bile flow could be redirected from the duodenum into the terminal ileum. The Meyer device required surgical insertion, diverted the fluids to the body surface and was not endoscopically insertable. In crossover studies in dogs, terminal direction of bilopancreatic drainage caused weight loss. Loss of 5-7% body mass occurred within the week-long time blocks of pancreaticobiliary diversion. The Herrera fistula device that was used in U.S. Pat. No. 5,322,697 is formed of stainless steel, requires invasive surgery and includes a port that exits the body through an incision in the abdomen. Neither this device, nor any similar device, was proposed for any therapeutic purpose.

Several reports regarding surgical pancreaticobiliary diversion but without noting effect upon body weight are known: Konturek, S. J. and Dubiel, J. (1969) *Effect of diversion of bile and pancreatic juice on pentagastrin-produced duodenal ulcers in cats*, Scand J Gastroenterol 4, 59-64; Abtahi, F. S. and Djahanguiri, B. (1975) *Decreased incidence of indomethacin-induced gastric ulceration in rats by bile duct diversion*, Br J Surg 62, 113-4, 1975; Konturek, S. J. and Thor, P. (1973) *Effect of diversion and replacement of bile on pancreatic secretion*, Am J Dig Dis 18, 971-7; Hara, H., Narakino, H. and Kiriyama, S. (1994) *Enhancement of pancreatic secretion by dietary protein in rats with chronic diversion of bile-pancreatic juice from the proximal small intestine*, Pancreas 9, 275-9; Dowling, R. H., Mack, E. and Small, D. M. (1970) *Effects of controlled interruption of the enterohepatic circulation of bile salts by binary diversion and by ileal resection on bile salt secretion, synthesis, and pool size in the rhesus monkey*, J Clin Invest 49, 232-42; Hughes, S. J., Behms, K. E. and Sarr, M. G. (1993) *Chronic bile diversion does not alter canine interdigestive myoelectric activity*, Dig Dis Sci 38, 1055-61; Linke, C. (1951) *The effect of diversion of bile to various parts of the intestine*, Surg Forum 94, 179-83; Rhodes, J., Davies, H. A., Wheeler, M. H., Psaila, J., Newcombe, R. G., Jones, J. M. and Bloom, S. (1984) *Bile diversion from the duodenum: its effect on gastric and pancreatic function*, Scand J Gastroenterol Suppl 92, 221-3; Takahashi, M., Naito, H., Sasaki, I., Funayama, Y., Shibata, C. and Matsuno, S. (2004) *Long-term bile diversion enhances basal and duodenal oleate-stimulated pancreatic exocrine secretion in dogs*, Tohoku J Exp Med 203, 87-95; Borgstrom, B. (1953) *On the mechanism of the intestinal fat absorption. V. The effect of bile diversion on fat absorption in the rat*, Acta Physiol Scand 28, 279-86; Li, Y., Hao, Y. and Owyang, C. (1995) *Evidence for autoregulation of cholecystokinin secretion during diversion of bile pancreatic juice in rats*, Gastroenterology 109, 231-81. Where body weight was measured following pancreaticobiliary bypass, one paper reported an increase in body weight (Levan, V. H. and Green, G. M. (1986) *Effect of diversion of bile-pancreatic juice to the ileum on pancreatic secretion and adaptation in the rat*, Proc Soc Exp Biol Med 181, 139-43). Others noted a decrease in body weight. Doty, J. E., Gu, Y. G. and Meyer, J. H. (1988) *The effect of bile diversion on satiety and fat absorption from liquid and solid dietary sources*, J Surg Res 45, 537-43 (Doty et al. 1988) reported a reduction in food intake. Kurosawa, H., Miyasaka, K. and Kitani, K. (1989) *Influence of bile flow obstruction versus bile diversion on pancreatic secretion in the conscious rat*, Int J Pancreatol 4, 187-97 (Kurosawa et al. 1989) reported an 8 g/day weight loss in rats, a rate comparable to that seen with full bile duct ligation. Ohisson, B., Yusa, T., Rehfeld, J. F., Lundquist, I., Ihse, I. and Axelson, J. (2000) *Effects of intraluminal trypsin and bile on the exocrine and endocrine pancreas after pancreaticobiliary diversion and biliodigestive shunt*, Pancreas 20, 170-6 reported final weights of 247 vs. 329 g (a 25% reduction in body weight over 4 weeks vs. controls) in rats where bile was diverted to mid ileum (Ohisson et al. 2000). Hara, H. and Kiriyama, S. (1991) *Responses of the exocrine pancreatic secretion to spontaneous feeding in rats with bile-pancreatic juice diversion*, Proc Soc Exp Biol Med 198, 732-6 reported a 25% reduction in rate of weight gain over 6 days (Hara and Kiriyama, 1991), and Takahashi et al. reported a 7% weight loss over 12 weeks in dogs (Takahashi et al. 2004).

Most of the foregoing references were investigating effects of bile on fat absorption, or were investigating the feedback control of pancreatic enzyme secretion. Due to the nature of the surgery involved in those preparations, it is also difficult to determine if the weight loss, where it was noted, was of a beneficial nature, or whether it was the result of post-operative cachexia. None of the authors suggested a role for bile acids or other bile/pancreatic constituents as signals to promote enteroendocrine secretion as in the invention. None proposed the use of such a principal as a therapeutic approach to obesity, and none proposed the use of a device to achieve that end such as in the present invention.

CLINICAL EXAMPLE

Figure 4A:
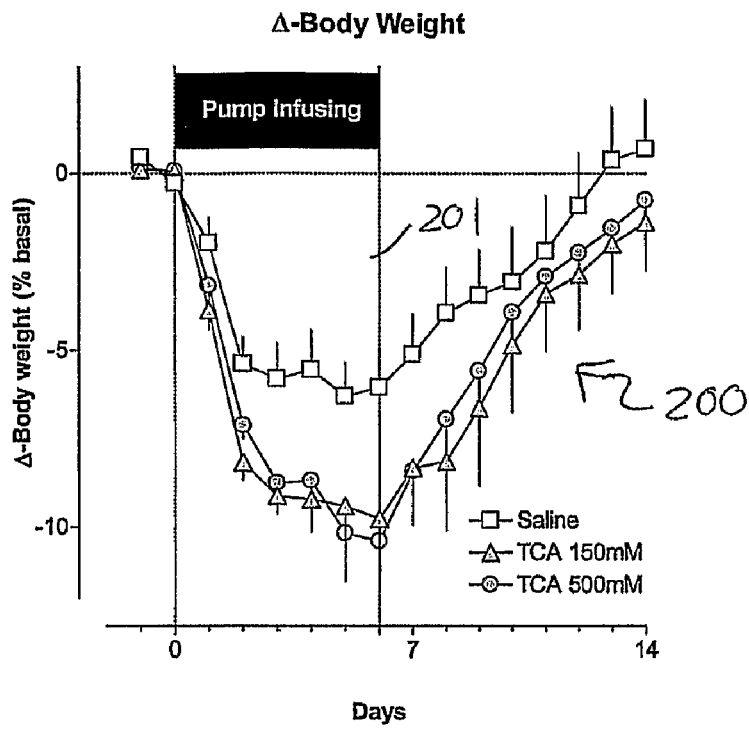
FIGS. 4A and 4B are graphs showing effects of intraduodenal bile salts on body weight and food intake in an animal, respectively.
Figure 4B:
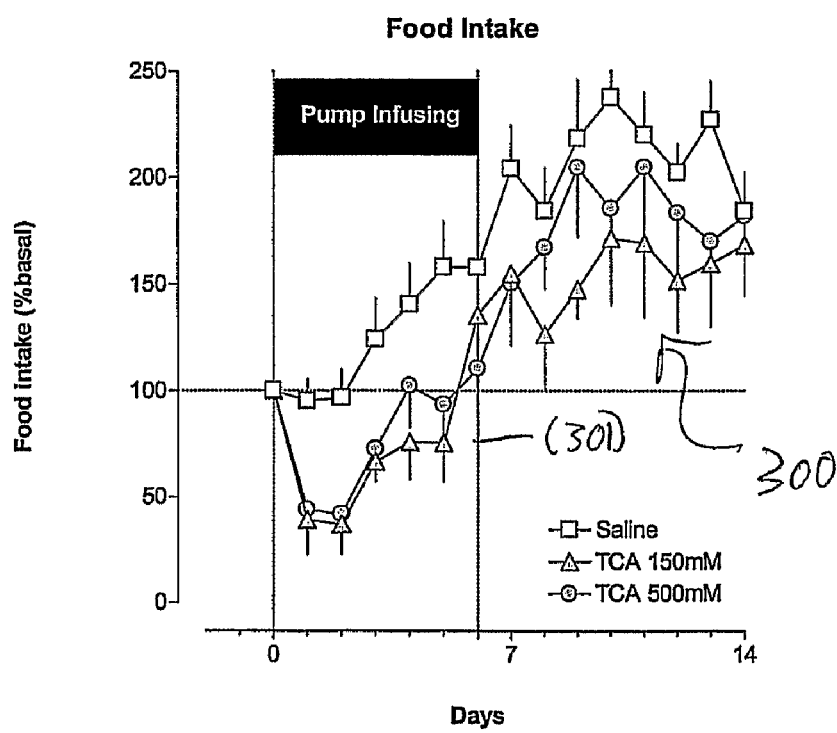

According to one clinical example, the effect of exogenous intraduodenal bile salt infusion on food intake and body weight was studied. Rats were surgically implanted with a catheter that passed from the peritoneal cavity to the lumen of the mid-duodenum and was held in place with a purse string suture and tissue adhesive. The peritoneal end of the catheter was connected to a mini-osmotic pump Alzet 2ML1 that delivered vehicle (controls; n=6), or solutions of taurocholic acid (150 mM (n=6) or 500 mM (n=7)) at a rate of 10 µL/hr for 1 week. The minipumps were primed for 24 hours before implantation, so the solution was therefore delivered into the duodenum for 6 days before the pumps stopped infusing. Relative to control rats, those infused with bile acid showed a reduction in food intake and in body weight, when expressed as a fraction of values prior to infusion. FIGS. 4A and 4B show this graphically.

FIG. 4A is a graphical illustration 200 showing loss of body weight as a function of number of days of pump infusing and shows a decrease in body weight when solutions of taurocholic acid were infused up until day 6 (201) when the pumps stopped infusing. FIG. 4B is a graphical illustration 300 shows the reduction in food intake resulting from infusion of tauricholic acid as a function of number of days of infusion and generally shows reduced food intake compared to the period after day 6 (301).

From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention. Applicant reserves the right to physically incorporate into this specification any and all materials and information from any such patents, applications, publications, scientific articles, web sites, electronically available information, and other referenced materials or documents. Applicant reserves the right to physically incorporate into any part of this document, including any part of the written description, the claims referred to above including but not limited to any original claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features reported and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims. Other embodiments are within the following claims.

What is claimed is:

1. A shunt device comprising:
   a catheter that facilitates transfer of bile from the gall bladder or the liver to a distal location of the gut, the catheter comprising:
   (i) a proximal end comprising an entry port and having an outer diameter that is sized to be positioned at the common bile duct or in the gall bladder of an animal;
   (ii) a terminal end comprising an exit port and further comprising an incorporated weight or a gravimetrically dense portion that facilitates positioning and residence of the terminal end to the distal location of the gut that is distally further along the digestive tract than the anatomical entry location of bile in the gut; and
   (iii) a lumen extending between the entry port and the exit port;
   wherein the catheter is configured to receive bile flow and not pancreatic flow.

2. A shunt device comprising:
   a catheter that facilitates transfer of bile from the gall bladder or the liver to a distal location of the gut, the catheter comprising:
   (i) a proximal end comprising an entry port and having an outer diameter that is sized to be positioned at the common bile duct or in the gall bladder of an animal;
   (ii) a terminal end comprising an exit port adapted to be positioned at a distal location of the gut that is distally further along the digestive tract than the anatomical entry location of bile in the gut; and
   (iii) a lumen extending between the entry port and the exit port;
   wherein the catheter is non-collapsible and comprises wires, ribs, or stiffening or semi-rigid materials, extending longitudinally along a length thereof, and is configured to receive bile flow and not pancreatic flow.

3. The shunt device as in claim 1 or 2, wherein the catheter isolates the bile from enteroendocrine cells lining the gut until the bile reaches the distal location.

4. The shunt device as in claim 1 or 2, wherein the entry port is adapted to be positioned in the gall bladder.

5. The shunt device as in claim 1 or 2, wherein an external wall of the catheter is adapted to be positioned in conterminous relationship with an inner surface of the common bile duct.

6. The shunt device as in claim 5, further comprising a stent having an expanded diameter greater than the inner diameter of the common bile duct that applies radially outward pressure to maintain the conterminous relationship between the external wall of the cathether and the inner surface of the common bile duct.

7. The shunt device as in claim 1 or 2, wherein the shunt device is further adapted to allow a portion of bile flow or at least one further endogenous secretion to flow outside of the catheter in an unobstructed manner.

8. The shunt device as in claim 7, wherein the at least one further secretion comprises pancreatic fluid.

9. The shunt device as in claim 6, wherein the stent is disposed within or along the catheter.

10. The shunt device as in claim 1 or 2, wherein the distal location is a location within the duodenum, the jejunum, the ileum, or the colon.

11. The shunt device as in claim 1 or 2, wherein the distal location is within the jejunum.

12. The shunt device as in claim 1 or 2, wherein the distal location comprises a plurality of locations including at least a first distal location and a second distal location.

13. The shunt device as in claim 1, wherein the catheter further comprises wires, ribs, or stiffening or semi-rigid materials extending longitudinally along a length thereof.

14. The shunt device as in claim 1 or 2, further comprising an anchoring member adapted to maintain the catheter in fixed position within the animal's anatomy.

15. The shunt device as in claim 14, wherein the anchoring member comprises an expansile component, memory metal, penetrating device, or spring loaded anchoring system.

16. The shunt device as in claim 15, wherein the expansile component is a balloon.

17. The shunt device as in claim 15, wherein the memory metal is nitinol.

18. The shunt device as in claim 14, wherein the anchoring member comprises barbs or prongs.

19. The shunt device as in claim 1 or 2, wherein the terminal end comprises a plurality of exit ports adapted to deliver the bile to different distal locations.

20. The shunt device as in claim 1 or 2, wherein the entry port of the catheter is adapted to be positioned in the gall bladder and the catheter further comprises an anchoring member adapted to maintain the catheter in a fixed position.

21. The shunt device as in claim 20, wherein the plurality of anchoring members comprises at least a first anchoring member adapted to be positioned at the throat of the gall bladder and a second anchoring member adapted to be positioned in the gut lumen.

22. The shunt device as in claim 1 or 2, wherein the catheter includes portions formed of radio-opaque materials.

23. The shunt device as in claim 1 or 2, wherein the catheter comprises a material impervious to chyme, the bile and further physiological fluids.

24. The shunt device as in claim 1 or 2, wherein the shunt device is adapted to be positioned in the animal with an endoscopic device.

25. The shunt device as in claim 1 or 2, wherein the shunt device is adapted to be fully contained inside the animal.

26. The shunt device as in claim 1 or 2, wherein the catheter comprises an inner diameter of about 2 mm to about 30 mm.

27. The shunt device as in claim 1 or 2, wherein the catheter comprises an inner diameter of about 3 mm to about 20 mm.

28. The shunt device as in claim 1 or 2, wherein the catheter comprises an inner diameter that progressively increases from the proximal end to the terminal end.

29. The shunt device as in claim 1 or 2, wherein an internal surface of the lumen comprises a material that minimizes aggregation of particulate matter or colonization by bacteria.

30. An endoscopically insertable shunt device comprising:
a conduit that facilitates transfer of bile from the gall bladder or the liver to a distal location of the gut, the conduit comprising:
(i) a proximal end comprising an entry port and having an outer diameter that is sized to be positioned at the common bile duct or in the gall bladder of an animal;
(ii) a terminal end comprising an exit port and further comprising an incorporated weight or a gravimetrically dense portion that facilitates positioning of the terminal end to the distal location of the gut that is distally further along the digestive tract than the anatomical entry location of bile in the gut; and
(iii) a lumen extending between the entry port and the exit port;
wherein the catheter is configured to receive bile flow and not pancreatic flow.

* * * * *

UNITED STATES PATENT AND TRADEMARK OFFICE
CERTIFICATE OF CORRECTION

PATENT NO. : 8,366,650 B2
APPLICATION NO. : 12/084069
DATED : February 5, 2013
INVENTOR(S) : Andrew Young It is certified that error appears in the above-identified patent and that said Letters Patent is hereby corrected as shown below:

Title Page, item (54), Title:

replace "BILIARY/PANCREATIC SHUNT DEVICE AND METHOD FOR TREATMENT OF METABOLIC AND OTHER DISEASES"

with -- BILIARY SHUNT DEVICE AND METHOD FOR TREATMENT OF METABOLIC AND OTHER DISEASES --

Signed and Sealed this
Twelfth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,366,650 B2
APPLICATION NO. : 12/084069
DATED : February 5, 2013
INVENTOR(S) : Andrew Young It is certified that error appears in the above-identified patent and that said Letters Patent is hereby corrected as shown below:

Title Page, item (54) and at Column 1, lines 1-3, Title:

replace "BILIARY/PANCREATIC SHUNT DEVICE AND METHOD FOR TREATMENT OF METABOLIC AND OTHER DISEASES"

with -- BILIARY SHUNT DEVICE AND METHOD FOR TREATMENT OF METABOLIC AND OTHER DISEASES --

This certificate supersedes the Certificate of Correction issued March 12, 2013.

Signed and Sealed this
Ninth Day of April, 2013

Teresa Stanek Rea
*Acting Director of the United States Patent and Trademark Office*